United States Patent [19]

Toner

[11] Patent Number: 5,488,960
[45] Date of Patent: Feb. 6, 1996

[54] CORONARY SINUS CATHETER INTRODUCER SYSTEM

[75] Inventor: E. Scott Toner, Vernon Hills, Ill.

[73] Assignee: Abbott Laboratories, Abbott Park, Ill.

[21] Appl. No.: 226,143

[22] Filed: Apr. 11, 1994

[51] Int. Cl.⁶ ................................................. A61M 25/00
[52] U.S. Cl. .......................... 128/772; 128/657; 604/264
[58] Field of Search ................................. 128/657, 772; 604/269, 272, 280, 281, 282, 171, 164

[56] References Cited

U.S. PATENT DOCUMENTS

| | | | |
|---|---|---|---|
| 4,616,652 | 10/1986 | Simpson | 128/772 X |
| 5,106,377 | 4/1992 | Martin | 604/281 X |
| 5,109,830 | 5/1992 | Cho | 604/281 X |
| 5,131,406 | 7/1992 | Kaltenbach | 128/772 |
| 5,299,574 | 4/1994 | Bower | 604/281 X |
| 5,306,254 | 4/1994 | Nash et al. | 128/772 X |

FOREIGN PATENT DOCUMENTS 454264  10/1991  European Pat. Off. ............... 604/281

Primary Examiner—Sam Rimell
Attorney, Agent, or Firm—T. M. Breininger; H. G. Thibault

[57] ABSTRACT

A coronary sinus catheter introducer system in which an introducer is installed in the right atrium of the cardiovascular system of a patient for delivery of a coronary sinus catheter into the coronary sinus. A bend near the distal end of the introducer enables placement of the end of the introducer into the coronary sinus opening and within the coronary sinus. A soft pliable tip end provided on the introducer minimizes abrasion of the coronary sinus and its opening by the introducer.

26 Claims, 7 Drawing Sheets

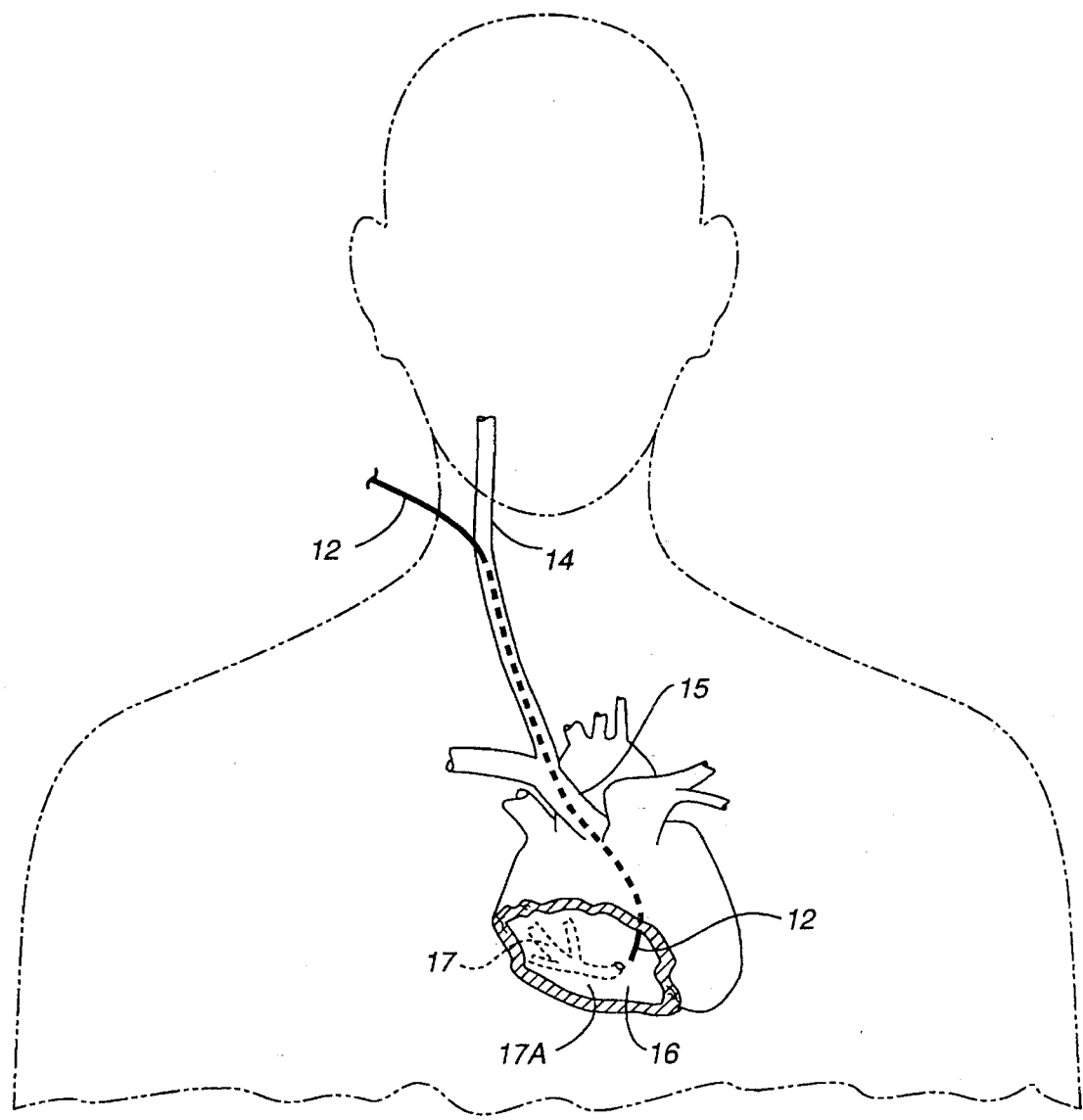
FIG._1

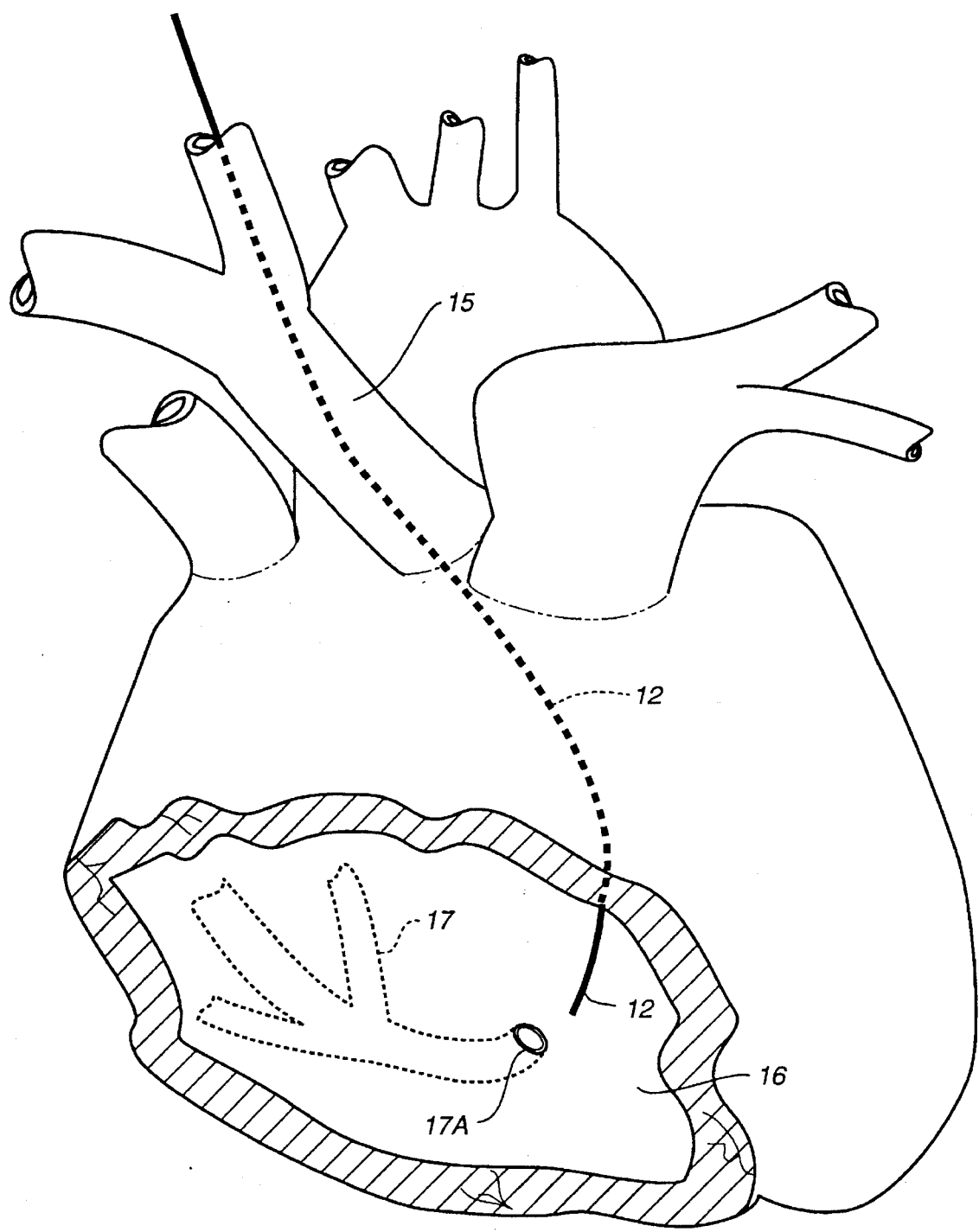
FIG._2

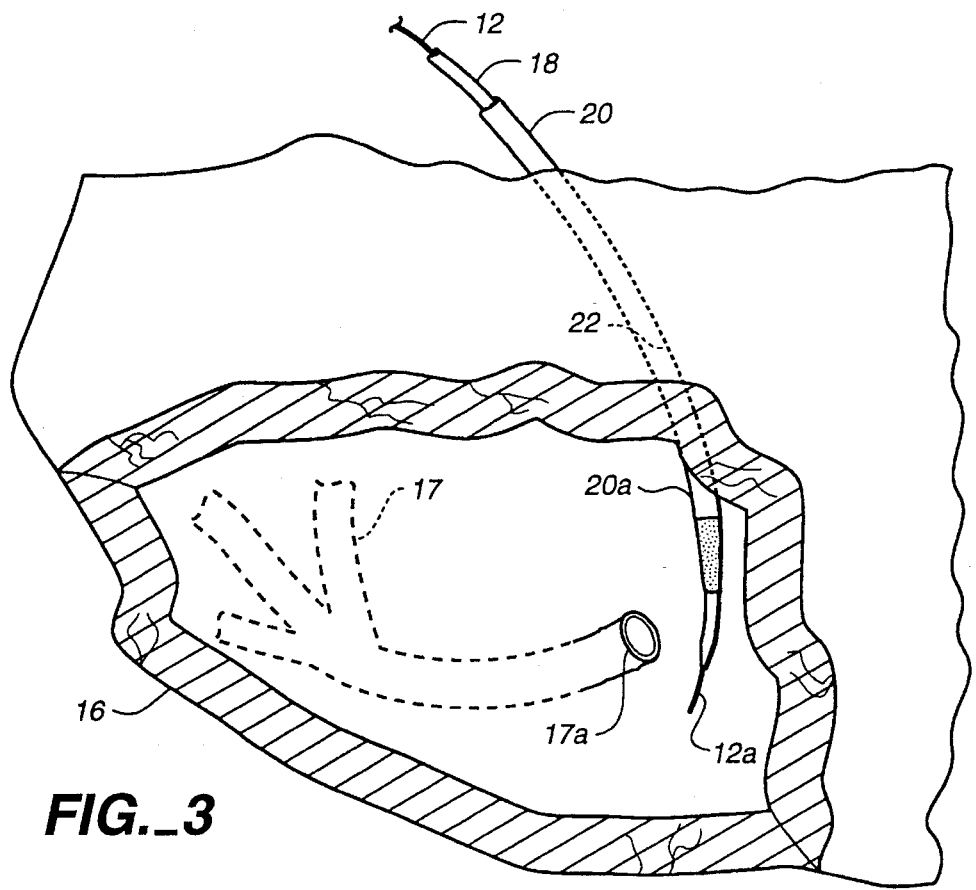
FIG._3
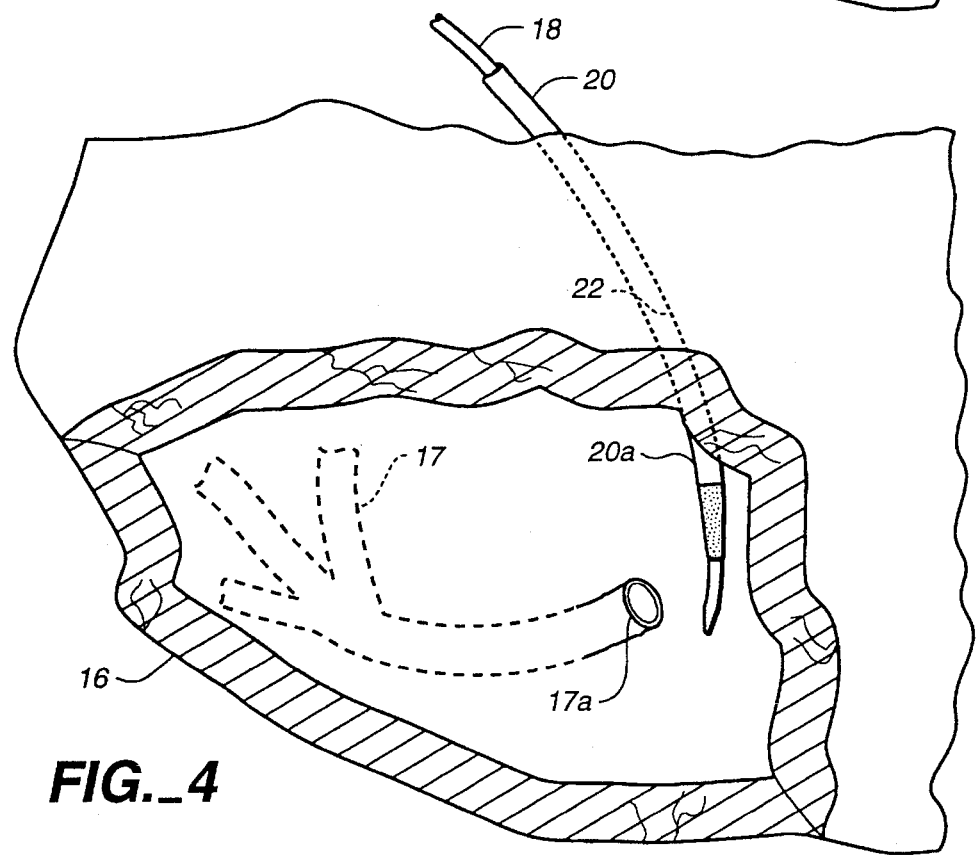
FIG._4

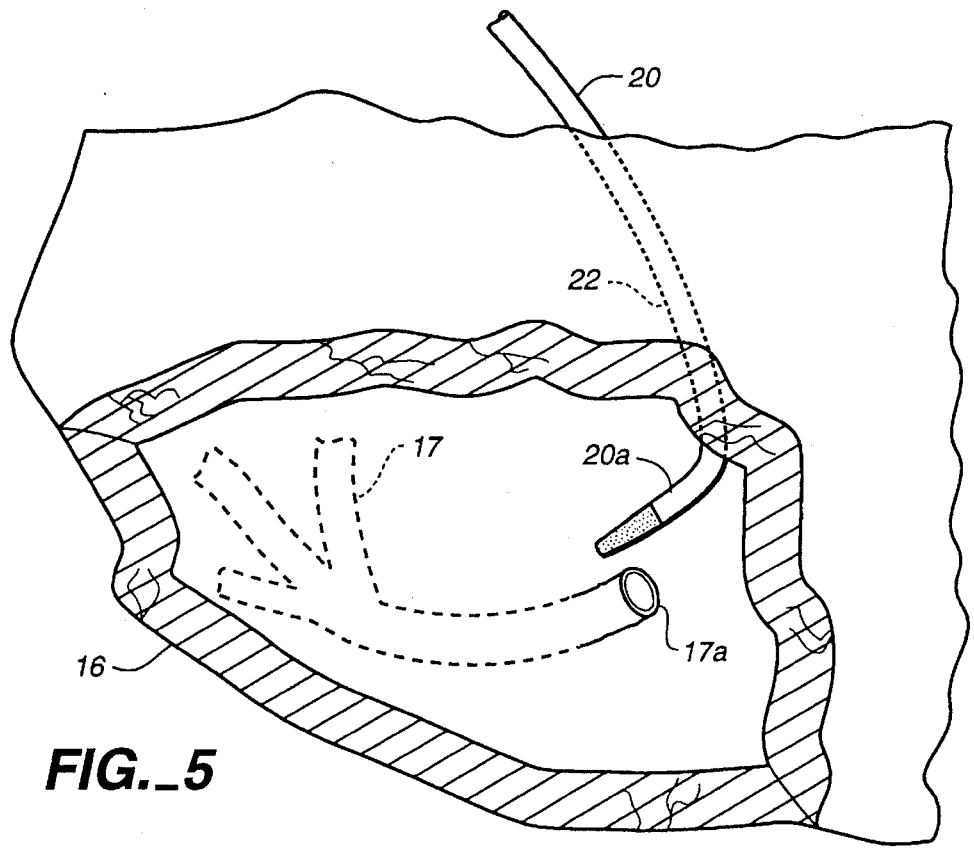
FIG._5
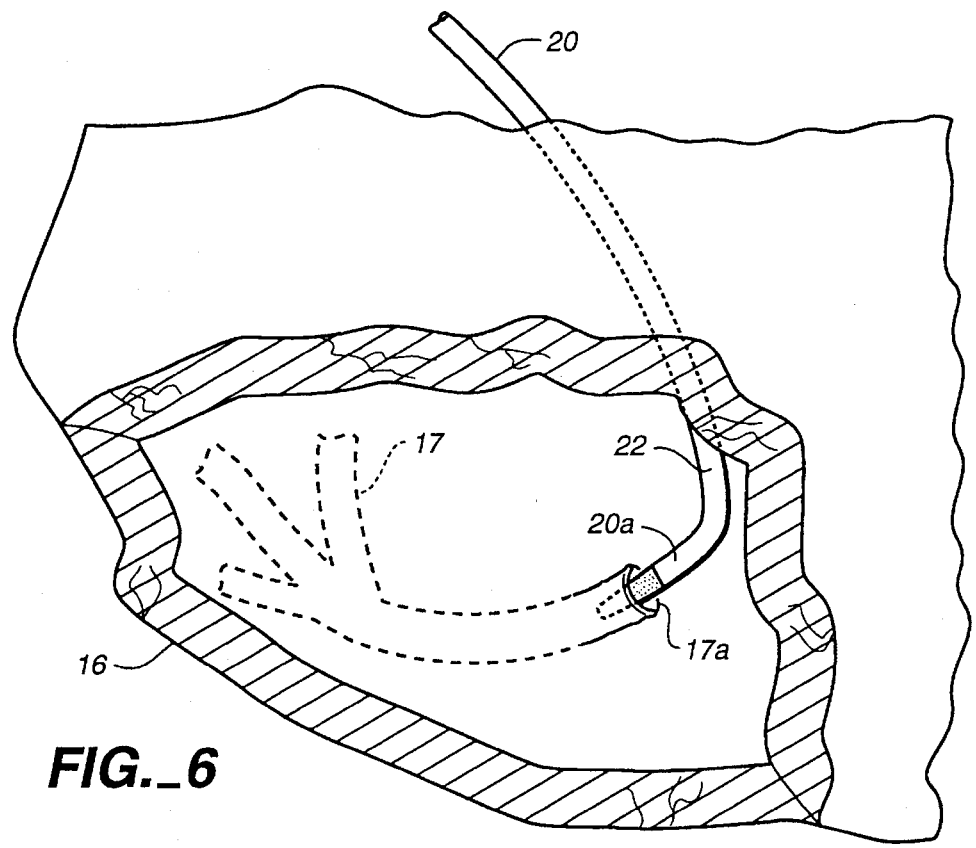
FIG._6

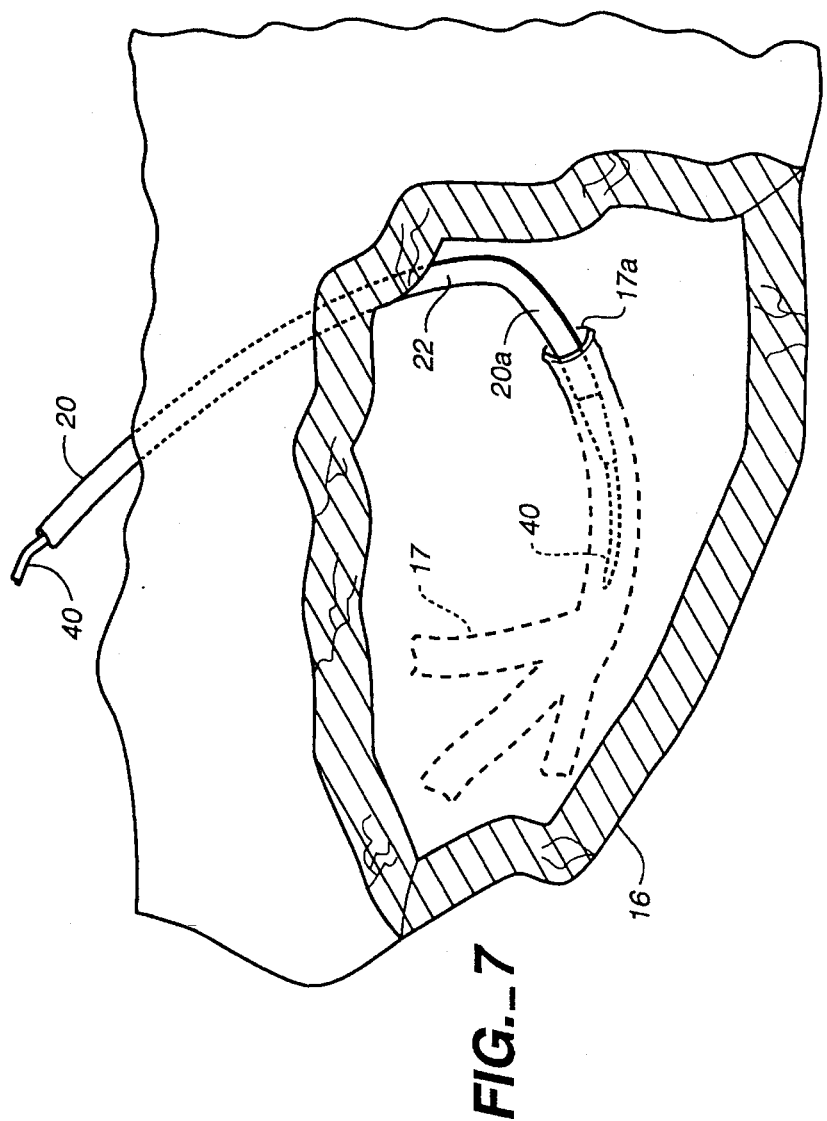
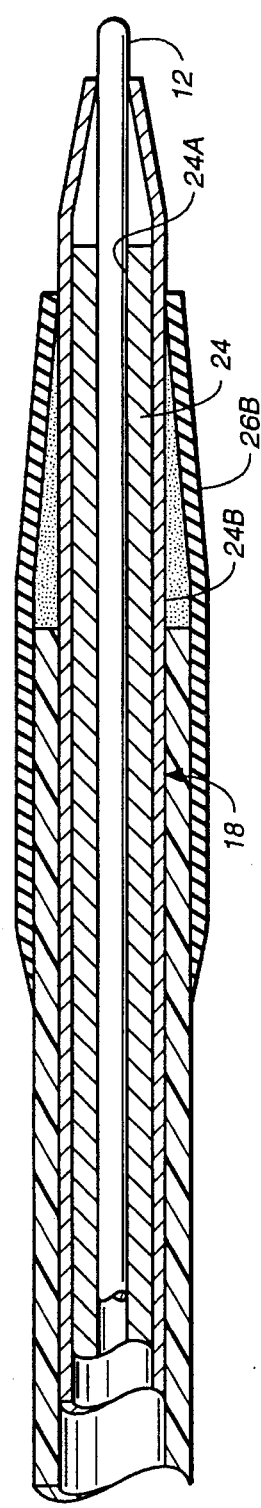

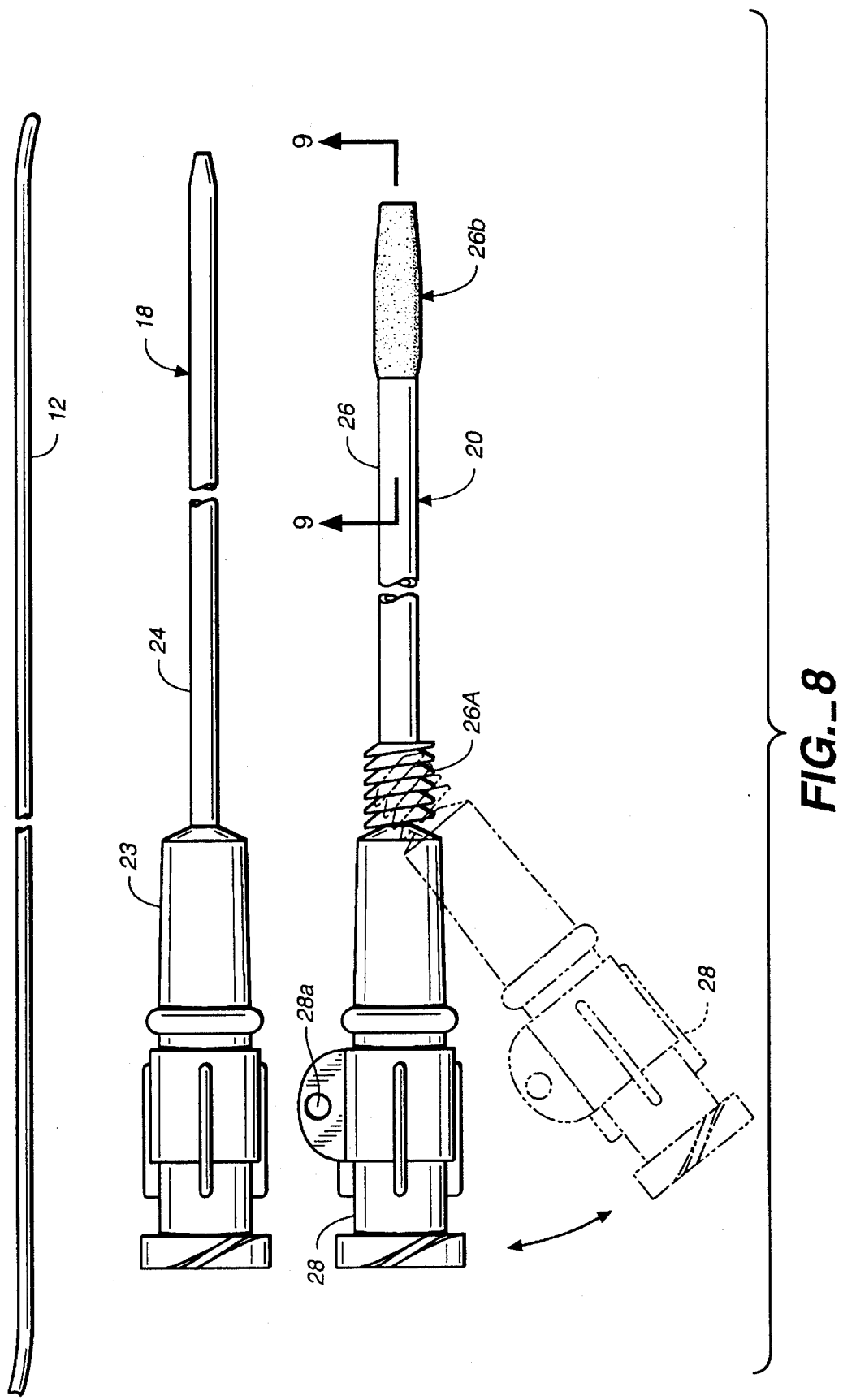
FIG._8

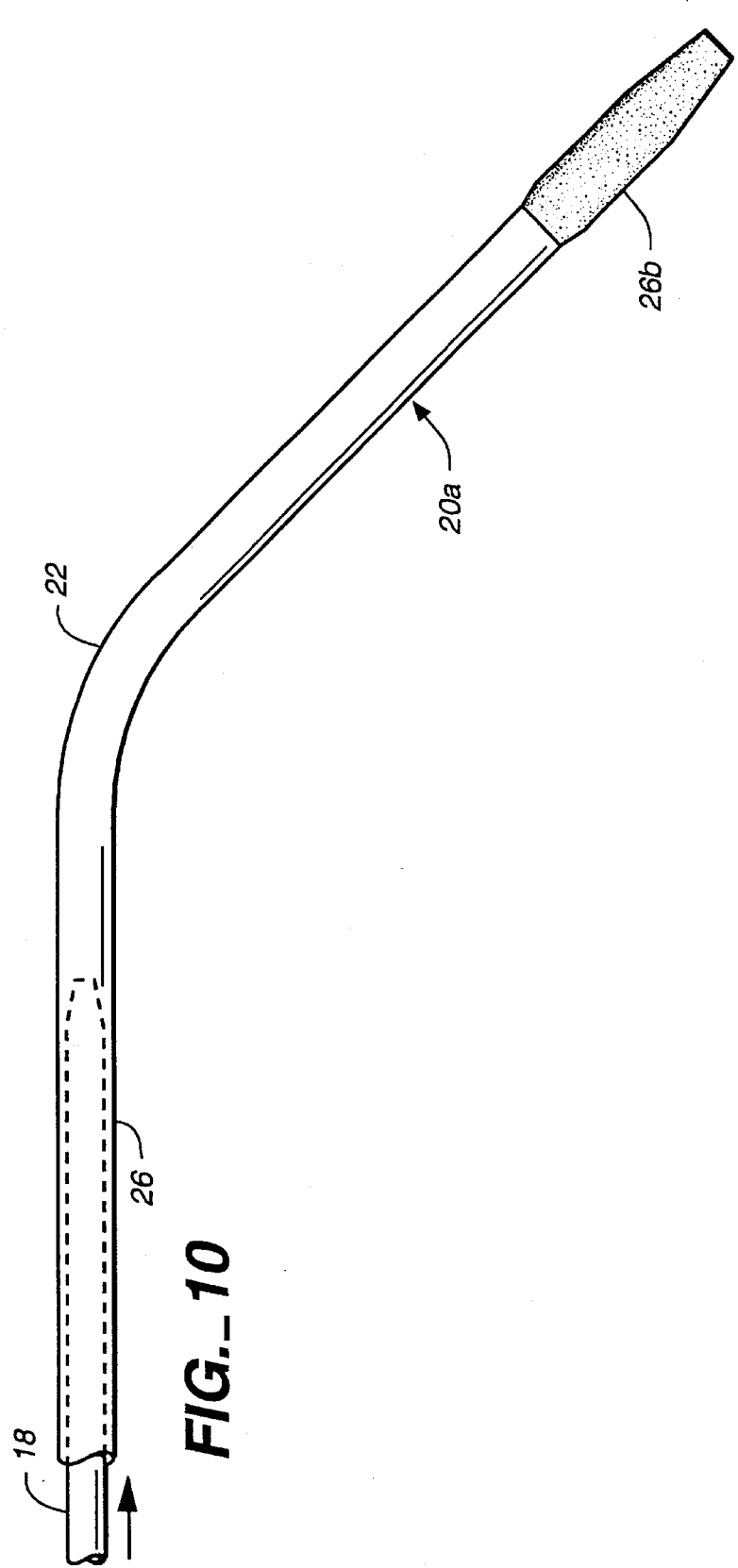
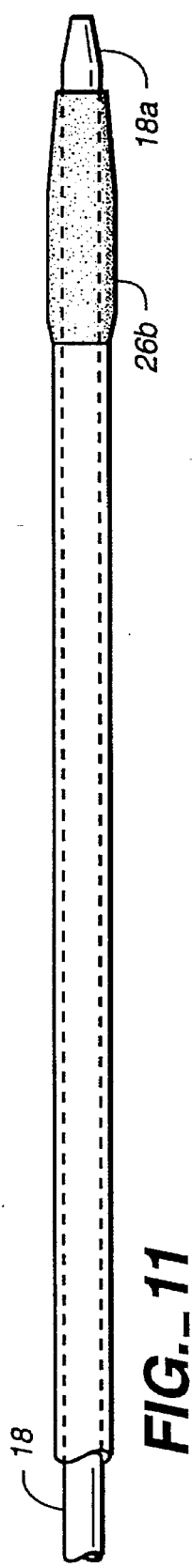

5,488,960

CORONARY SINUS CATHETER INTRODUCER SYSTEM

BACKGROUND OF THE INVENTION

The present invention relates to medical devices for introducing catheters or the like into the cardiovascular system of the body.

Catheter introducers provide a conduit for passage of catheters and other medical devices, for example, guide wires, through the body flesh into a blood vessel or other body passage way. In a typical situation, when a catheter introducer is used, a guide wire is placed in the body to align the introducer within the main vein in which it is being placed. A dilator/introducer combination is then passed over the guide wire. Once the introducer has been advanced to its end position, the dilator and guide wire are removed, and then the catheter is passed down the introducer to its desired end position within the body of the patient.

Introducers are used in various organs of the body. For example, in the surgical removal of the gall bladder or cholecystectomy; i.e., a cholangiography catheter is placed into the cystic duct by means of the cholangiography catheter inserter described in U.S. Pat. No. 5,167,645. U.S. Pat. No. 5,098,393 describes a medical device for introducing catheters or the like into blood vessels of the body. Flexible catheters used in the cardiovascular system, for example a guiding catheter of variable, operator-controlled flexibility to be used in the performance of a percutaneous translumenal coronary angioplast procedure is described in U.S. Pat. Nos. 4,822,325 and 4,909,787, a guiding catheter of some complexity is also shown in U.S. Pat. No. 4,759,748, and a guide which can be introduced into a narrow passage in a human or other animal body is described in U.S. Pat. No. 5,131,406.

However, none of the above noted catheters include a catheter guide system nor do any of the particular guides described incorporate features which place the catheter introducer within the coronary sinus of the cardiovascular system prior to the cardiac procedure to be performed within the body.

SUMMARY OF THE INVENTION

By contrast the coronary sinus catheter introducer system of the present invention operates within the cardiovascular system to specifically guide the introducer into the coronary sinus of the cardiovascular system, enables the introduction of a coronary sinus catheter through the introducer and into the coronary sinus, with the introducer remaining in place during the coronary procedure to be monitored by the coronary sinus catheter.

To be operative with the coronary sinus catheter, the coronary sinus introducer includes a bend at its lower end that better enables the introducer to be placed within the coronary sinus. The coronary sinus catheter introducer system also includes a dilator which enables placement of the catheter introducer into the cardiovascular system, and also includes a means for enabling the introducer to engage a guide wire placed in the cardiovascular system.

These and other features of the invention will be seen from the following description of the preferred embodiment and from the claims, and should be considered with the drawings provided with such description for a better understanding of the invention.

BRIEF DESCRIPTION OF THE DRAWINGS

FIG. 1 is a schematic representation of the placement of a guide wire into the cardiovascular system of a patient;

FIG. 2 is a detail of FIG. 1 in which the heart of FIG. 1 is enlarged;

FIG. 3 is a detail of FIG. 2 in which the coronary sinus catheter introducer system of the present invention places the coronary sinus introducer within the patient in the vicinity of the coronary sinus;

FIG. 4 is a figure similar to FIG. 3 in which the guide wire has been removed from the coronary sinus catheter introducer system;

FIG. 5 is a figure similar to FIG. 4 in which the dilator of the coronary sinus catheter introducer system of the present invention has been removed;

FIG. 6 is a figure similar to FIG. 5 in which the coronary sinus catheter introducer now resides within the coronary sinus of the patient;

FIG. 7 is a figure similar to FIG. 6 in which the coronary sinus catheter is now disposed within the coronary sinus of the patient;

FIG. 8 is an elevational view of the separate elements of the coronary sinus catheter introducer system of the present invention;

FIG. 9 is a sectional view of the assembled coronary sinus catheter introducer system taken along lines 8—8 of FIG. 7;

FIG. 10 is a detail of the coronary sinus catheter introducer system showing the bend in the coronary sinus introducer prior to the placement of the dilator therein;

FIG. 11 is a detail similar of FIG. 9 with the dilator of the coronary sinus catheter introducer system of the present invention fully placed within the coronary sinus introducer.

DETAILED DESCRIPTION OF THE PREFERRED EMBODIMENT

The present invention is best understood by first starting with a description of the environment in which the invention operates. As shown in FIGS. 1 and 2, to place the coronary sinus introducer 20 of the present invention in the body, it is first required that a guide wire 12 be inserted into the jugular vein 14 to travel along the jugular vein to the superior vena cava 15 of the heart and into the right atrium 16 and into the vicinity of the coronary sinus 17 at the coronary sinus opening 17a within the right atrium.

The guide wire 12 is placed in the jugular vein 14 through the use of the Seldinger technique. This technique may be used for gaining arterial or venous access. It involves locating the vessel by palpation and entering it with a locator needle through the skin (percutaneous insertion). Once the vessel is entered, the guide wire 12 is inserted through the needle (not shown) and the needle is removed. This procedure can be done quickly, does not require surgical incision and preserves the site of insertion for future procedures.

The superior vena cava returns blood from the upper half of the body, and opens into the upper and posterior part of the atrium. Its orifice is directed downward and forward and has no valve. The coronary sinus 17 returns the greater part of the blood from the substance of the heart. Its opening 17a is placed between the orifice of the inferior vena cava and the atrioventricular opening, and is protected by a thin, semi-circular valve, termed the valve of the coronary sinus, which covers the lower part of the orifice. It prevents the regurgitation of blood into the sinus during the contraction of the atrium. This valve may be double or it may be cribriform.

Placement of the coronary sinus introducer 20 of the present invention is best seen through the series of FIGS. 3 through 7. As shown in FIG. 3, the guide wire 12 is first introduced into the cardiovascular system through the jugular vein 14 and then through the superior vena cava 15 to place its distal end in the vicinity of the coronary sinus opening 17a.

Then the dilator 18 receives the coronary introducer 20 in a manner to be described in more detail below, then the dilator and introducer combination descend along the guide wire 12 through the jugular vein 14, through the superior vena cava 15 and into the right atrium 16 to the position shown in FIG. 3 in which the guide wire 12 with its distal end 12a, the dilator 18 with its tip or distal end 18a and the introducer 20 with its tip or distal end 20a are all in the right atrium in the vicinity of the coronary sinus opening 17a.

In FIG. 4 guidewire 12 has been removed from the combination of dilator 18 and introducer 20 to leave dilator tip end 18a and introducer end 20a in the vicinity of the coronary sinus opening 17a within the right atrium 16.

In FIG. 5 coronary sinus introducer 20 with its tip end 20a is shown in the right atrium. Introducer 20 is bent at bend or bent section 22 to place tip end 20a of the introducer in the vicinity of the coronary sinus opening 17a. In FIG. 5 the dilator 18, which is a relatively stiff straight member, has been removed from the coronary sinus introducer 20 and the bent section 22 has been restored to the coronary sinus introducer to tilt it toward the opening 17a of the coronary sinus 17 and to enable the introducer tip end 20a to be placed within the coronary sinus 17 as shown in FIG. 6. In FIG. 7 a coronary sinus catheter 40 has been delivered into the coronary sinus of the patient.

The structure of the coronary sinus catheter introducer system of the present invention is best understood by references to FIGS. 8–11. At the top of FIG. 8 is shown the guide wire 12 which is essentially a long metallic coiled wire preferably made of a metal which will not interact with body fluids, such as stainless steel. As shown in FIGS. 8 and 9, dilator 18 is a relatively stiff member having a luer fitting 23 at one end with a longitudinal rod 24 extending from the luer fitting 22. The longitudinal rod 24 is approximately 30–40 centimeters inches in length and is preferably made of a material which will not interact with body fluids such as a relatively stiff polyurethane material. The rod 24 includes a central longitudinal bore 24a. The rod 24 receives a coating 24b, also preferably made of a material non-reactive with body fluids, such as polyurethane. The dilator 18 is relatively inflexible, and is expected to follow a path from the jugular vein 14, into the superior vena cava 15 and thereafter into the right atrium 16 of the heart. The luer fitting 23 receives an end cap (not shown) during installation of the dilator-introducer combination in the right atrium to minimize blood loss therethrough.

The introducer 20 comprises a longitudinal tubular main body portion 26 having a luer fitting 28 at a proximal end thereof. Similarly, the luer fitting 28 receives an end cap (not shown) which may be received following removal of the guide wire and dilator and prior to catheter installation to minimize blood loss through the tube 26. Luer fitting 28 also includes an eyelet 28a for a purpose to be described later. The main body portion 26 is a relatively inflexible longitudinal plastic tube having a pleated section 26a at its proximal end to give some flexibility to the introducer 20 at the junction at the tube 26 and the luer fitting 28. Also a soft plastic bumper 26b is provided at the distal end of the plastic tube 26 to prevent abrasive contact between the coronary sinus 17 and the coronary sinus opening 17a and the introducer 20 when the distal end 20a of the introducer 20 is placed within the coronary sinus 17.

The bend 22 at the distal end 20a of the coronary sinus introducer 20 is shown in more detail in FIG. 10. The distal end 20a of the introducer 20 includes the bumper 26b and extends about 2–4 centimeters beyond the bent section 22 at an angle between 30°–45° from the longitudinal axis of the tube 26.

It is the purpose of the dilator 18 to take the bend 22 out of the introducer 20 during the placement of the coronary sinus introducer within the body of the patient as shown in FIGS. 3–7. Therefore, as shown in FIG. 11, when the dilator 18 is fully extended to place its tip end 18a beyond the bumper 26b at the distal end of the tube 26, the tube 26 is fully aligned along its longitudinal axis to remove the bend 22 from the introducer 20. Moreover there is a tight tolerance between the pliable bumper 26b of the introducer 20 and the dilator 18 to minimize blood loss to the patient through the interface between the dilator outer face and the inner face of the introducer body.

When the dilator 18 is removed from the coronary sinus introducer 20, the bend 22 returns to the coronary sinus introducer to enable placement of its end 20a in the coronary sinus opening 17a.

Although the invention has been described with reference to the preferred embodiment, other embodiments can achieve the same results. Variations and modifications of the present invention will be obvious to those skilled in the art and it is intended to cover in the apended claims all such modifications and equivalents. The entire disclosures of all applications, patents, and publications cited above, and of the corresponding application are hereby incorporated by reference.

We claim:

1. An introducer system for delivery of a coronary sinus catheter, said system comprising:

a guide wire having a proximal and a distal end;

an introducer comprising a tube having a longitudinal main body portion and opposite ends, an open distal end of the introducer to be installed adjacent the coronary sinus opening in the cardiovascular system of a patient and an opposite open end to be disposed at a surface jugular entry point, said introducer of resilient material and having a pre-determined bend adjacent a distal end section thereof to better position said open distal introducer end in the vicinity of the coronary sinus opening; and a longitudinal dilator having a bore to receive the guide wire wherein, the dilator is placed in the introducer to remove said pre-determined bend and align said distal end section with the main body portion during installation, the guide wire is delivered into the cardiovascular system to dispose its distal end in the right atrium, the introducer is installed on the dilator to provide a dilator-introducer combination, said combination then descends along the guide wire and into the right atrium, then the guide wire and the dilator member are removed following introducer installation to restore said pre-determined bend in the distal end section of the introducer to position the open distal end of the introducer in the vicinity of the coronary sinus opening, and a coronary sinus catheter is delivered through the introducer and into the coronary sinus of the patient.

2. An introducer system for delivery of a coronary sinus catheter, said system comprising:

a guide wire having opposite ends;

an introducer including a linear main body portion comprising a tube having opposite ends, an open distal end of the introducer to be installed adjacent the coronary sinus opening in the cardiovascular system of a patient and an opposite open end to be disposed at a surface jugular entry point, said introducer of resilient material and having a pre-determined bend adjacent a distal end section; and a dilator installed in the introducer to remove said pre-determined bend and align said distal end section with the main body portion during installation, wherein the guide wire is delivered into the cardiovascular system to dispose a distal end thereof in the right atrium, the introducer and dilator descend along the guide wire and into the right atrium, the guide wire and dilator are removed to restore said pre-determined bend in the distal end section of the introducer to position the open distal introducer end in the vicinity of the coronary sinus opening following introducer installation and the coronary sinus catheter is delivered through the introducer and into the coronary sinus of the patient.

3. The system is claimed in claim 2 wherein the dilator includes a longitudinal core having a central bore therein.

4. The system is claimed in claim 3 wherein a sheath overlies the core of the dilator.

5. The system is claimed in claim 4 wherein the sheath of the dilator comprises a polyurethane material.

6. The system is claimed in claim 5 wherein the dilator includes a luer fitting in its proximal end.

7. The system is claimed in claim 1 wherein the introducer includes a flexible bumper at its distal end to minimize abrasion in the engagement of the end of the introducer with the coronary sinus and the coronary sinus opening.

8. The system is claimed in claim 7 wherein the introducer includes a luer fitting at its proximal end.

9. The system is claimed in claim 8 wherein an accordion pleat is disposed in the tube at the junction of the luer fitting and said proximal end to provide added flexibility to the introducer.

10. The system is claimed in claim 9 wherein the luer fitting on the introducer includes an eyelet for suturing the luer fitting of the introducer to the patient.

11. An introducer system for delivery of a coronary sinus catheter, said system comprising:

an introducer comprising a tube having a longitudinal main body portion and opposite ends, an open distal end of the introducer to be installed adjacent the coronary sinus opening in the cardiovascular system of a patient and an opposite open end to be disposed at a surface jugular entry point, said introducer of resilient material and having a pre-determined bend adjacent a distal end section thereof in the installed position to better position said introducer in the vicinity of the coronary sinus opening; and a longitudinal dilator member placed in the introducer to remove said pre-determined bend and align said distal end section with the main body portion during installation, wherein the introducer is installed on the dilator to provide a dilator-introducer combination, said combination then descends into the right atrium, then the dilator member is removed following introducer installation to restore said pre-determined bend in the distal end section of the introducer to position the open distal end of the introducer in the vicinity of the coronary sinus opening, and a coronary sinus catheter is delivered through the introducer and into the coronary sinus of the patient.

12. The system is claimed in claim 11 wherein the dilator includes a longitudinal core having a central bore therein.

13. The system is claimed in claim 12 wherein a sheath overlies the core of the dilator.

14. The system is claimed in claim 13 wherein the sheath of the dilator comprises a polyurethane material.

15. The system is claimed in claim 14 wherein the dilator includes a luer fitting in its proximal end.

16. The system is claimed in claim 11 wherein the introducer includes a flexible bumper at its distal end to minimize abrasion in the engagement of the end of the introducer with the coronary sinus and the coronary sinus opening.

17. The system is claimed in claim 11 when the introducer includes a luer fitting at its proximal end.

18. The system is claimed in claim 17 wherein an accordion pleat is disposed in the tube at the junction of the luer fitting and said proximal end to provide added flexibility to the introducer.

19. The system as claimed in claim 18 wherein the luer fitting on the introducer includes an eyelet for suturing the luer fitting of the introducer to the patient.

20. An introducer system for delivery of a coronary sinus catheter, said system comprising:

an introducer including a tube having a longitudinal main body portion and opposite ends, an open distal end of the introducer to be installed adjacent the coronary sinus opening in the cardiovascular system of a patient and an opposite end to be disposed at a surface jugular entry point, said introducer of resilient material and having a pre-determined bend adjacent a distal end section to better position said open distal end of-the introducer in the vicinity of the coronary sinus opening; and a longitudinal straightening member placed in the introducer for removing pre-determined bend and aligning said distal end section with the main body portion during installation, wherein the introducer and said member descend into the cardiovascular system and into the right atrium, and following introducer installation, said straightening member is removed to restore said pre-determined bend in the distal end section of the introducer and position the introducer open distal end in the vicinity of the coronary sinus opening, and a coronary sinus catheter is delivered through the introducer and into the coronary sinus of the patient.

21. The system is claimed in claim 20 wherein the introducer includes a flexible bumper at its distal end to minimize abrasion in the engagement of the introducer with the coronary sinus and the coronary sinus opening.

22. The system is claimed in claim 21 when the introducer includes a luer fitting at its proximal end.

23. The system is claimed in claim 22 wherein an accordion pleat is disposed in the tube at the junction of the luer fitting and said proximal end to provide added flexibility to the introducer.

24. The system is claimed in claim 23 wherein the luer fitting on the introducer includes an eyelet for suturing the luer fitting of the introducer to the patient.

25. A method for delivery of a coronary sinus catheter, said method comprising:

providing a guide wire having a proximal and a distal end;

providing an introducer, said introducer comprising a tube having a longitudinal main body portion and opposite ends;

providing a bend near the distal end of the introducer to better position said introducer end in the vicinity of the coronary sinus opening;

providing a longitudinal dilator member having an internal bore to receive the guide wire;

placing the dilator in the introducer to align the bend with the main body portion during installation of the introducer in the cardiovascular system of a patient;

delivering the guide wire into the cardiovascular system to dispose its distal end in the right atrium;

lowering the dilator-introducer combination along the guide wire and into the right atrium to install one end of the introducer adjacent the coronary sinus opening and dispose an opposite end at a surface jugular entry point;

removing the guide wire and the dilator member following introducer installation to restore the bend and position the introducer end in the vicinity of the coronary sinus opening;

and delivering a coronary sinus catheter through the introducer and into the coronary sinus of the patient.

26. A method for delivery of a coronary sinus catheter, said method comprising:

providing a guide wire having opposite ends;

providing an introducer comprising a tube having a linear main body portion and opposite ends, and being of sufficient length to have one end of the introducer installed adjacent the coronary sinus opening in the cardiovascular system of a patient and an opposite end disposed at a surface jugular entry point;

providing said introducer with a bend adjacent said one end; installing a dilator member in the introducer to provide a dilator-introducer combination and to align said bend with the main body portion during installation;

delivering the guide wire into the cardiovascular system to dispose one end thereof in the right atrium;

lowering the dilator-introducer combination along the guide wire to dispose the one end thereof in the right atrium;

removing the guide wire and the dilator from the introducer to restore the bend therein to position the end of the introducer in the vicinity of the coronary sinus opening; and delivering the coronary sinus catheter through the introducer and into the coronary sinus of the patient.

* * * * *